US008753282B2

(12) United States Patent
Kukita et al.

(10) Patent No.: US 8,753,282 B2
(45) Date of Patent: Jun. 17, 2014

(54) BLOOD PRESSURE MEASUREMENT APPARATUS

(75) Inventors: Tomohiro Kukita, Amsterdam (NL); Koji Maruta, Joyo (JP); Masataka Yanagase, Osaka (JP)

(73) Assignee: Omron Healthcare Co., Ltd., Kyoto (JP)

( * ) Notice: Subject to any disclaimer, the term of this patent is extended or adjusted under 35 U.S.C. 154(b) by 228 days.

(21) Appl. No.: 13/159,064

(22) Filed: Jun. 13, 2011

(65) Prior Publication Data

US 2011/0245694 A1 Oct. 6, 2011

Related U.S. Application Data

(63) Continuation of application No. PCT/JP2009/070479, filed on Dec. 7, 2009.

(30) Foreign Application Priority Data

Dec. 12, 2008 (JP) ................................. 2008-317066

(51) Int. Cl.
*A61B 5/02* (2006.01)
(52) U.S. Cl.
USPC ........................................................ 600/490
(58) Field of Classification Search
USPC .................................................. 600/485–525
See application file for complete search history.

(56) References Cited

U.S. PATENT DOCUMENTS

| 2003/0013976 A1* | 1/2003 | Freund et al. ................. 600/503 |
| 2003/0171683 A1* | 9/2003 | Inagaki et al. ................ 600/499 |
| 2005/0187485 A1* | 8/2005 | Fumuro et al. ................ 600/499 |
| 2005/0192501 A1* | 9/2005 | Sano et al. .................... 600/499 |

FOREIGN PATENT DOCUMENTS

| JP | 01-254145 A | 10/1989 |
| JP | 2005-334049 A | 12/2005 |
| JP | 2006-000337 A | 1/2006 |
| JP | 3147041 U | 12/2008 |

OTHER PUBLICATIONS

International Search Report issued in PCT/JP2009/070479 mailed on Jan. 19, 2010, and English translation thereof, 2 pages.
Patent Abstracts of Japan, Publication No. 2006-000337, Publication Date: Jan. 5, 2006, 1 page.
Patent Abstracts of Japan, Publication No. 2005-334049, Publication Date: Dec. 8, 2005, 1 page.
Patent Abstracts of Japan, Publication No. 01-254145, Publication Date: Oct. 11, 1989, 1 page.

* cited by examiner

*Primary Examiner* — Michael Kahelin
*Assistant Examiner* — Mitchell Alter
(74) *Attorney, Agent, or Firm* — Osha Liang LLP

(57) ABSTRACT

A blood pressure measurement apparatus detects a downward flexure of an arm rest and informs a user of the downward flexure on a display unit. By providing a partially color changing display or a blinking display on the display unit, the user is informed that a measurement posture is not good. The blood pressure measurement apparatus has an elbow rest with an arrangement that can easily prompt the user to be in a good posture for measurement.

2 Claims, 10 Drawing Sheets

BLOOD PRESSURE MEASUREMENT APPARATUS

TECHNICAL FIELD

The present invention relates to a blood pressure measurement apparatus and, more specifically to, an upper arm type blood pressure measurement apparatus equipped with an automatic cuff winding mechanism that automatically winds a cuff around the upper arm.

BACKGROUND ART

Typically, a blood pressure value is measured by winding a cuff fitted with an organism compressing fluid bladder configured to compress the artery located in the organism around a body surface of the organism and then expanding and contracting the organism compressing fluid bladder to detect a resultant arterial pressure pulse wave.

It is to be noted that the cuff means a stripe-shaped structure that has a lumen and can be wound around part of the organism so that it can be utilized in measurement of an arterial pressure of the upper/lower limb by injecting a fluid such as an air or a liquid into the lumen. Therefore, the cuff is a word denoting a concept that includes an organism compressing fluid bladder and a winding member configured to wind the organism compressing fluid bladder around the organism.

The conventional upper arm type blood pressure measurement apparatus operates by winding a cuff around the upper arm of a user etc. such that fluctuations occur in the cuff winding strength for each measurement, also resulting in fluctuations in the measured value of the blood pressure. Accordingly, in recent years, such a blood pressure measurement apparatus has been widely used as to be equipped with an automatic cuff winding mechanism capable of automatically winding the cuff around the upper arm.

The blood pressure measurement apparatus equipped with the automatic cuff winding mechanism is fitted on its predetermined position with an upper arm insertion unit through which the upper arm can be axially inserted from its front side, so that a user may have the cuff wound around his upper arm only by axially inserting the upper arm from its front side through a hollow portion formed in the upper arm insertion unit. With this blood pressure measurement apparatus, a constant winding strength will be reproduced every time measurement is conducted, so that stable measurement accuracy can be realized and, moreover, a complicated winding operation can be eliminated.

As prior art technological documents disclosing such a blood pressure measurement apparatus equipped with the automatic cuff winding mechanism, the following Japanese Unexamined Patent Publication No. 2006-000337 (Patent Document 1) and Japanese Unexamined Patent Publication No. 2005-334049 (Patent Document 2) may be enumerated. By using those blood pressure measurement apparatuses, the blood pressure can be measured and managed every day for daily healthcare, so that a family-use blood pressure measurement apparatus is becoming widely used. By using such a blood pressure measurement apparatus, the blood pressure is measured every day to show timewise fluctuations in blood pressure so that it may be utilized in self-diagnosis against a risk of damage to the cardiovascular system.

Patent Document 1: Japanese Unexamined Patent Publication No. 2006-000337

Patent Document 2: Japanese Unexamined Patent Publication No. 2005-334049

SUMMARY OF INVENTION

In a blood pressure measurement apparatus disclosed in Japanese Unexamined Patent Publication No. 2006-000337 (Patent Document 1) or Japanese Unexamined Patent Publication No. 2005-334049 (Patent Document 2), an elbow rest is fitted to an upper arm insertion unit in order to reduce loads on a user. However, if the elbow rest is provided, there is a case where measurement may be conducted in a condition where excessive force is applied on the elbow rest, so that in such a case, correct results of measurement may not be obtained.

On the other hand, to prompt giving a good posture for measurement, such an arrangement may be possible as to provide the elbow rest with a pressure sensor configured to detect the elbow is mounted on the elbow rest. However, a position of the elbow cannot be detected in some cases because of individual differences in thickness and shape of the arm.

Further, there may be a case where a correct blood pressure value cannot be measured because the posture of a user goes bad when he has applied a weight on the entire arm in order to detect the position forcibly. Moreover, even in a case where the elbow is placed on the elbow rest properly, if the arm is bent in any direction, the blood pressure value cannot be measured accurately. In particular, if the arm is bent right or left, the artery is not properly compressed by the cuff, so that a correct blood pressure value may not be measured.

Therefore, one or more embodiments of the present invention provides a blood pressure measurement apparatus equipped with an elbow rest having a configuration that can easily prompt a user to keep a good posture for measurement.

A blood pressure measurement apparatus according to one or more embodiments of the present invention includes an upper arm insertion unit having a hollow portion through which an upper arm of a user is axially inserted from its front side, a main body portion to which the upper arm insertion unit is coupled, and an arm rest that has an elbow rest surface provided on an upper surface of the main body portion and an arm rest surface provided on a rear side of the elbow rest surface so that an arm of the user is mounted thereon.

According to one or more embodiments of the present invention, the arm rest has flexure detection means configured to detect downward flexure of the arm rest in a condition where the user's arm is mounted on the arm rest. This blood pressure measurement apparatus has informing means configured to inform the user that downward flexure of the arm rest is detected when the downward flexure of the arm rest is detected by the flexure detection means.

In a blood pressure measurement apparatus according to one or more embodiments of the present invention, if an elbow and an arm of a user are mounted on an elbow rest surface and an arm rest surface, respectively, in a condition where the user is in a good posture for measurement, an arm rest does not flex downward. However, if the user is not in the good posture for measurement, an unnecessary force is applied on the arm, resulting in a downward flexure of the arm rest. By detecting the downward flexure of the arm rest by using the flexure detection means, it is possible to inform the user of bad posture for measurement by using the informing means. As a result, the user is prompted to be in a good posture for measurement, so that correct blood pressure measurement results can be obtained.

DETAILED DESCRIPTION OF INVENTION

The following will describe in detail a blood pressure measurement apparatus according to one or more embodiments of the present invention with reference to the drawings. It is to be noted that the blood pressure measurement apparatus described below is equipped with an automatic cuff winding mechanism, which is used to wind a cuff around an upper arm.

Figure 1:
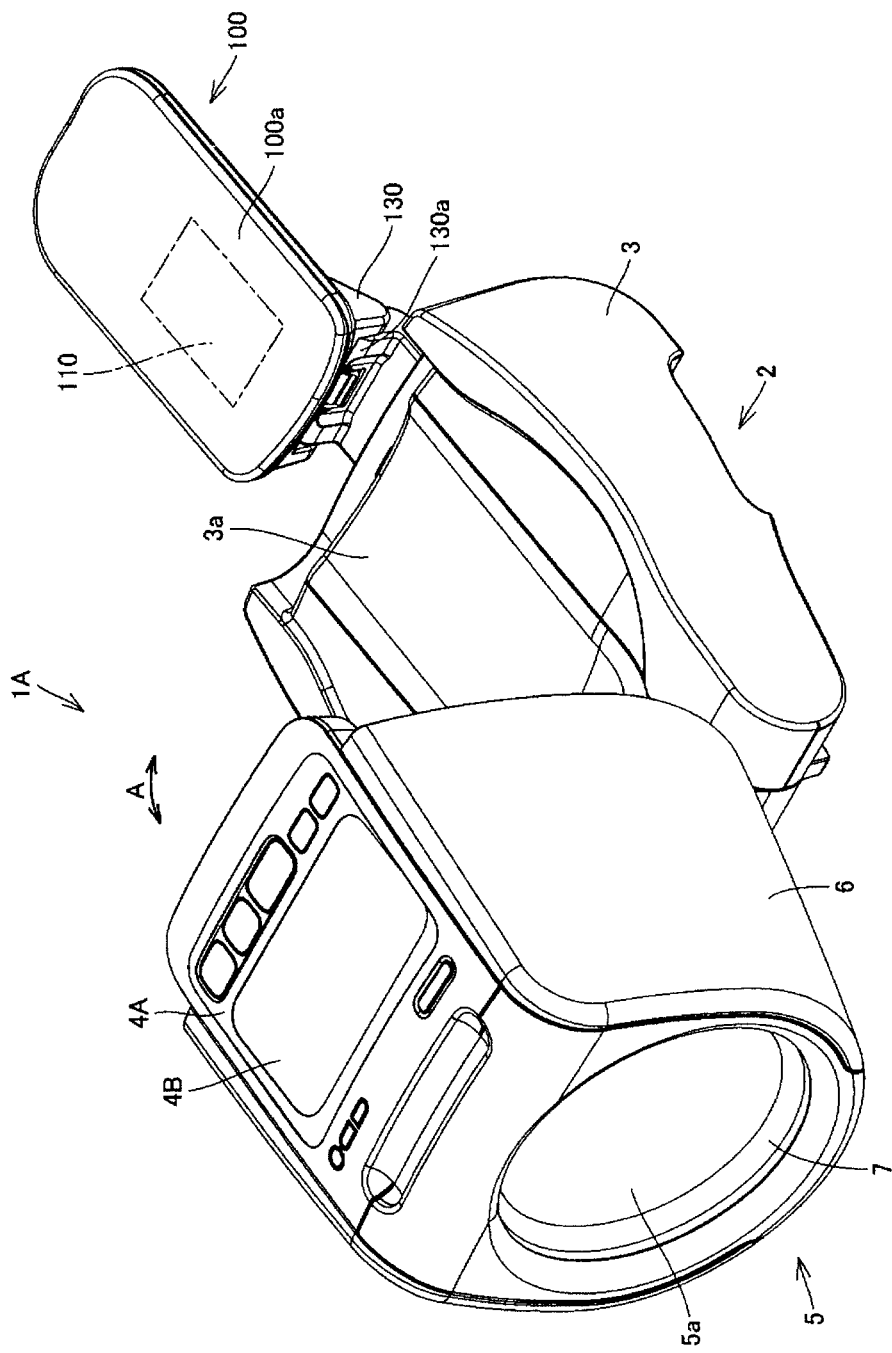
FIG. 1 is a perspective view of a blood pressure measurement apparatus as viewed from diagonally upward right according to one or more embodiments of the present invention.
Figure 2:
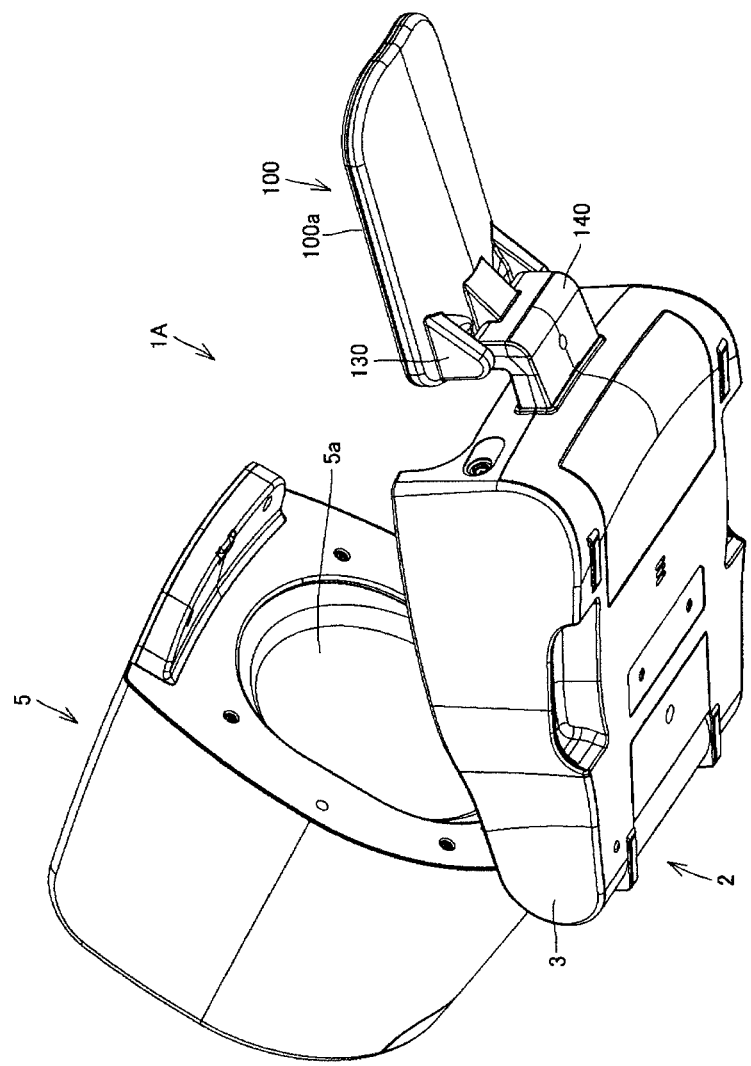
FIG. 2 is a perspective view of the blood pressure measurement apparatus as viewed from diagonally downward left according to one or more embodiments of the present invention.

FIGS. 1 and 2 are explanatory views of an external structure of the blood pressure measurement apparatus according to one or more embodiments of the present invention; FIG. 1 is a perspective view of the blood pressure measurement apparatus according to one or more embodiments of the present invention as viewed from diagonally upward right, and FIG. 2 is its perspective view as viewed from diagonally downward left. It is to be noted that FIG. 1 is a perspective view of a state in which an upper arm insertion unit is rotated to a position where the upper arm can be inserted, and FIG. 2 is a perspective view of a state in which the blood pressure measurement apparatus is not in use for measurement. First, a description will be given of an external configuration of the blood pressure measurement apparatus according to one or more embodiments of the present invention with reference to those figures.

(Configuration of Blood Pressure Measurement Apparatus 1A)

As shown in FIGS. 1 and 2, a blood pressure measurement apparatus 1A according to one or more embodiments of the present invention is equipped with a main body portion 2 mounted on a mount surface of a desk etc., and an upper arm insertion unit 5 having a hollow portion 5a through which an upper arm of a user is axially inserted from its front side. A main body portion 2 is covered with a main body portion casing 3 that mainly stores various air system components, a CPU, and the like.

On an upper surface of the main body portion casing 3, with being mounted on the mount surface, an elbow rest surface 3a is formed, which is inclined gradually in a back-and-forth direction (the front side is lower than the rear side) and curved in a right-and-left direction. It is to be noted that the front side in the back-and-forth direction means the side toward the user, and the rear side in the back-and-forth direction means the side away from the user in a condition where the user is using the apparatus (see FIGS. 6 and 7).

The upper arm insertion unit 5 includes an upper arm insertion unit casing 6 formed roughly like a cylinder as a tubular portion and a cuff 7 disposed on an inner periphery surface of the upper arm insertion unit casing 6. On a surface of the upper arm insertion unit casing 6, an operation unit 4A is provided on which a variety of buttons are disposed such as a power button for turning on a power supply, a measurement button for starting measurement, and a display unit operation button for operating a display unit. Further, roughly in a midsection region of the surface of the upper arm insertion unit casing 6, a display unit 4B is provided, which is configured to display results of measurement, an operation guide, etc.

The upper arm insertion unit 5 is coupled to the main body portion 2 on its front side in such a manner as to freely rotate in the back-and-forth direction by using a rotary coupling mechanism 2a including a rotary shaft. Specifically, the main body portion casing 3 and the upper arm insertion unit casing 6 are coupled to each other in such a manner as to freely rotate in an arrow direction in FIG. 1 around the rotary shaft as a rotary center, which shaft is incorporated in the main body portion casing 3 close to a forward end positioned toward the user in the main body portion 2.

(Arm Rest 100)

Moreover, on the rear side of the elbow rest surface 3a of the main body portion casing 3 of the blood pressure measurement apparatus 1A according to one or more embodiments of the present invention, an arm rest 100 is provided, which has an arm rest surface 100a on which the arm of the user is mounted. Like the elbow surface 3a, the arm rest surface 100a is inclined gradually in the back-and-forth direction (the front side is lower than the rear side) and curved in the right-and-left direction.

On a lower surface of the arm rest 100, a support plate 130 having a built-in rotary shaft 130a (see FIGS. 8 and 9) is provided, while a base member 140 configured to support the support plate 130 in such a manner as to freely rotate is coupled to a rear-side side surface of the main body portion casing 3 in an attachable-and-detachable manner.

(Flexure Detection Means 110)

The arm rest 100 is fitted with flexure detection means 110 configured to detect downward flexure of the arm rest 100 in a condition where the user's arm is mounted on the arm rest 100. The flexure detection means 110 can detect the downward flexure of the arm rest 100 because the arm rest 100 and the rotary shaft 130*a* incorporate microswitches and sensors such as an acceleration sensor, an angle sensor, and a magnetic sensor. FIG. 1 shows a case where a substrate 110 is provided that has the acceleration sensor mounted in the arm rest 100.

(Operations of Arm Rest 100)

Figure 3:
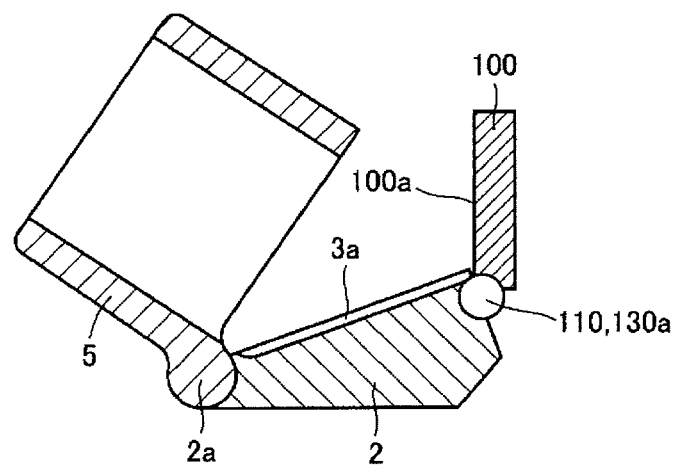
FIG. 3 is a diagram showing a state where an arm rest surface of an arm rest of the blood pressure measurement apparatus has come close to an elbow rest surface with respect to a main body portion around a rotary shaft according to one or more embodiments of the present invention.

Next, a description will be given of operations of the arm rest 100 with reference to FIGS. 3 and 4. FIG. 3 shows a state where the arm rest surface 100*a* of the arm rest 100 has come close to the elbow rest surface 3*a* with respect to the main body portion 2 around the rotary shaft 130*a*, and FIG. 4 shows a state where the arm rest 100 has moved rotatingly (in a rotating direction denoted by an arrow B in FIG. 4) around the rotary shaft 130*a* to such a position that the arm rest surface 100*a* and the elbow rest surface 3*a* may be roughly in plane with each other.

Figure 4:
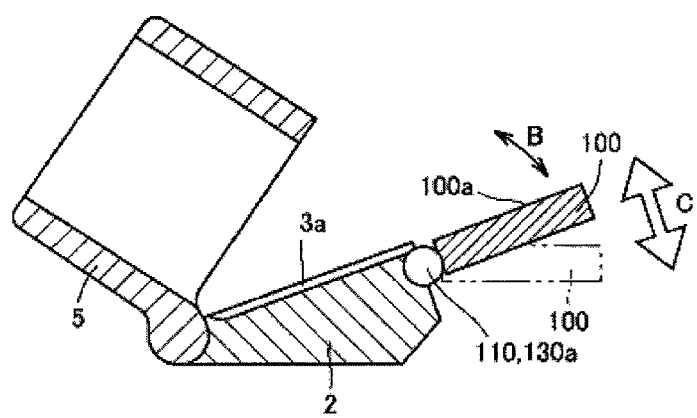
FIG. 4 is a diagram showing a state where the arm rest has moved rotatingly around the rotary shaft to such a position that the arm rest surface and the elbow rest surface of the blood pressure measurement apparatus may be roughly in plane with each other according to one or more embodiments of the present invention.

In an ordinary blood pressure measurement state, a blood pressure of the user is measured by using a position where the arm rest surface 100*a* and the elbow rest surface 3*a* are roughly in plane with each other as a reference position as shown in FIG. 4. If the user's posture is not good, an unnecessary force is applied on the user's arm, resulting in a downward flexure of the armrest 100 (in a rotating direction around the rotary shaft 130*a* denoted by an arrow C in FIG. 4). The downward flexure of the arm rest 100 is detected by the flexure detection means 110.

(Function Blocks of Blood Pressure Measurement Apparatus 1A)

Figure 5:
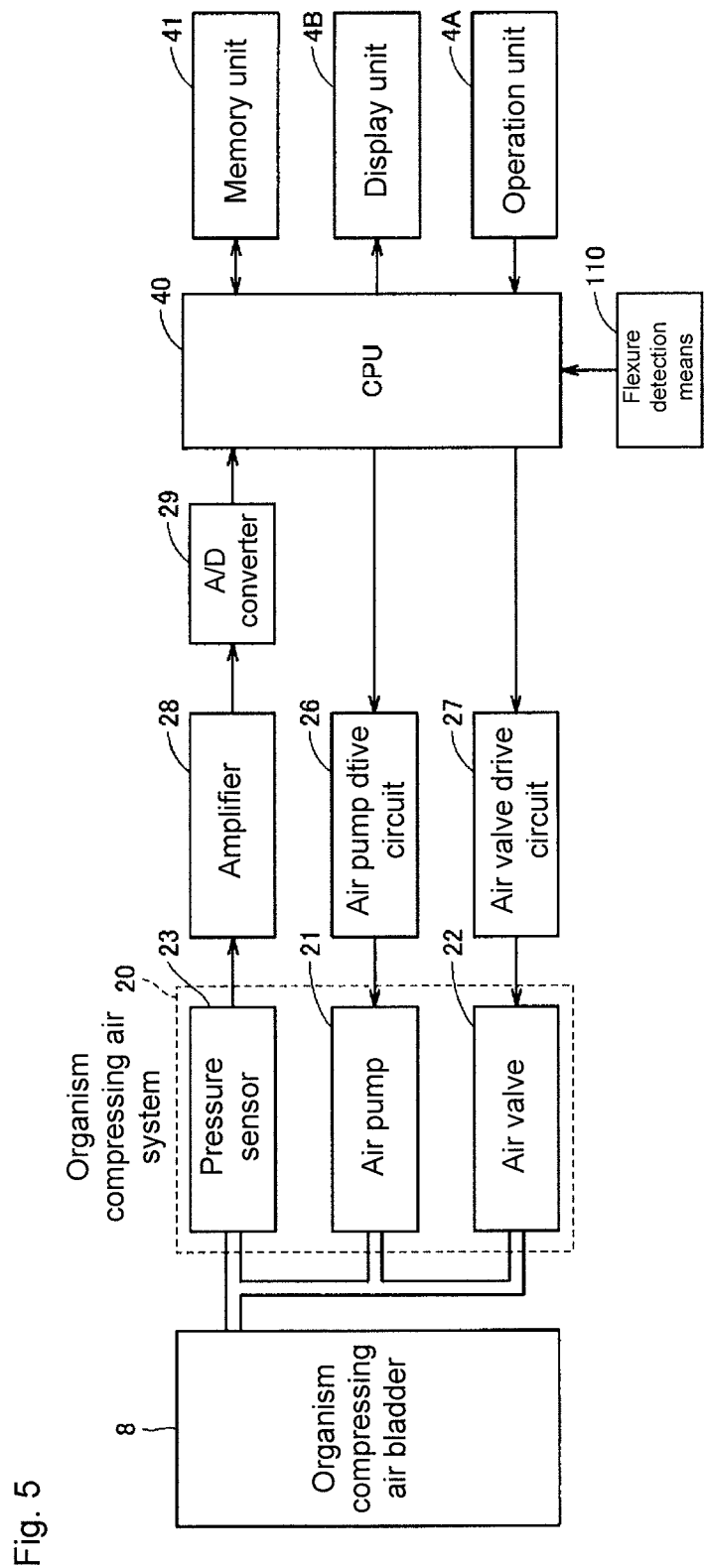
FIG. 5 is a diagram showing one example of function blocks of the blood pressure measurement apparatus according to one or more embodiments of the present invention.

Next, a description will be given of function blocks of the blood pressure measurement apparatus 1A with reference to FIG. 5 according to one or more embodiments of the present invention. FIG. 5 is a diagram showing one example of the function blocks of the blood pressure measurement apparatus according to one or more embodiments of the present invention. It is to be noted that the function blocks of the blood pressure measurement apparatus 1A are not limited to those shown in FIG. 5. As shown in FIG. 5, an organism compressing air bladder 8 included in the cuff is connected to an organism compressing air system 20 with an air tube. Further, the organism compressing air system 20 is controlled in operation by a CPU 40.

The organism compressing air system 20 includes an air pump 21, an air valve 22, and a pressure sensor 23. The air pump 21 is means configured to pressurize the lumen of the organism compressing air bladder 8. The air pump 21 is driven by an air pump drive circuit 26 supplied with commands from the CPU 40, to feed compressed air to the lumen of the organism compressing air bladder 8 so that a pressure of the lumen of the organism compressing air bladder 8 becomes a predetermined pressure at the time of measurement.

The air valve 22 is means configured to keep or decrease the pressure of the lumen of the organism compressing air bladder 8. The opening/closing motion of the air valve 22 is controlled by an air valve drive circuit 27 supplied with the commands from the CPU 40, to keep and decrease the pressure of the lumen of the organism compressing air bladder 8 if this pressure is high due to the air pump 21 at the time of measurement and return this lumen of the organism compressing air bladder 8 back to the atmospheric pressure after measurement.

The pressure sensor 23 is means configured to detect the pressure of the lumen of the organism compressing air bladder 8. The pressure sensor 23 detects the pressure of the lumen of the organism compressing air bladder 8, which varies momentarily during measurement, and supplies an amplifier 28 with a signal that corresponds to the detected value. The amplifier 28 amplifies the signal provided from the pressure sensor 23 and outputs it to an ND converter 29. The ND converter 29 converts the analog signal supplied from the amplifier 28 into a digital signal and outputs it to the CPU 40.

The CPU 40 controls the organism compressing air system 20 based on the commands input to the operation unit 4A provided at the main body portion 2 of a sphygmomanometer and outputs results of measurement to the display unit 4B and a memory unit 41. It is to be noted that the memory unit 41 is configured to store the measurement results.

Further, the CPU 40 is supplied with a signal from the flexure detection means 110, so that if having received the signal from the flexure detection means 110, the CPU 40 informs the user on the display unit 4B that downward flexure of the arm rest 100 is detected.

In the blood pressure measurement apparatus 1A according to one or more embodiments of the present invention, all of the function blocks shown in FIG. 5 except for the organism compressing air bladder 8, the pressure sensor 23, and the flexure detection means 110 are stored in the main body portion casing 3.

(Procedure for Attaching Cuff in Blood Pressure Measurement Apparatus 1A)

Figure 6:
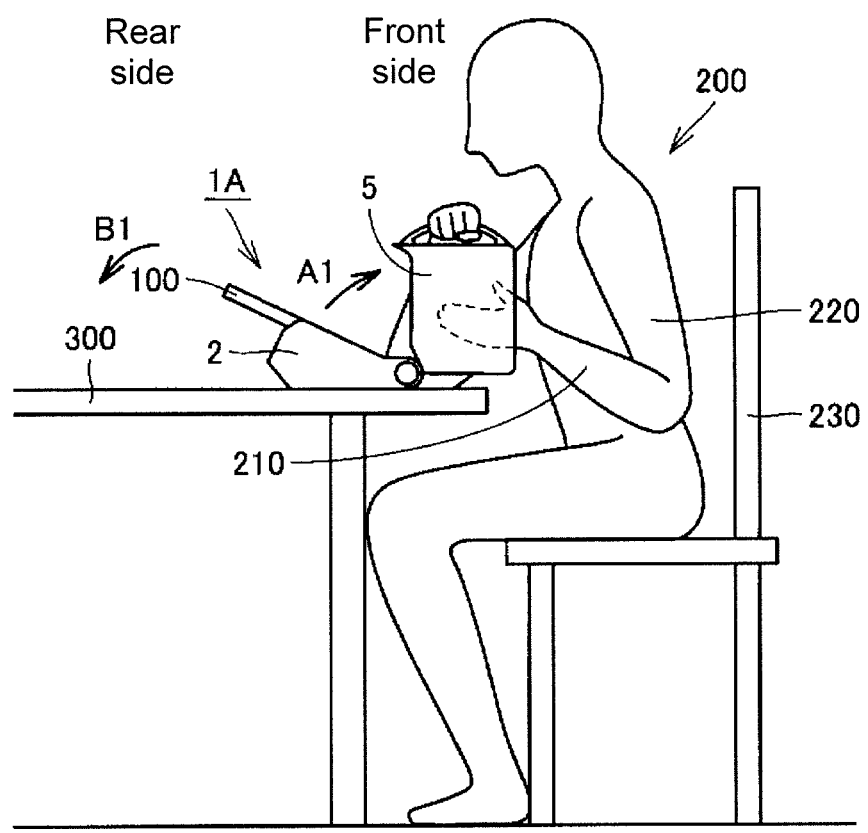
FIG. 6 is a schematic diagram showing a procedure for attaching a cuff in the blood pressure measurement apparatus according to one or more embodiments of the present invention.
Figure 7:
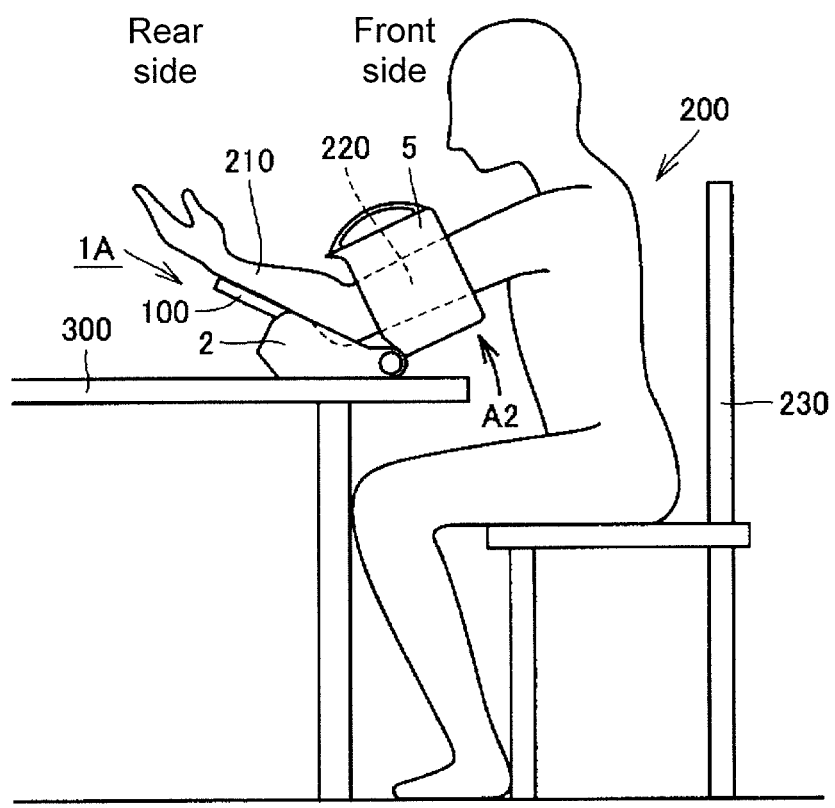
FIG. 7 is a schematic diagram showing a posture for measurement after the cuff is attached in the blood pressure measurement apparatus according to one or more embodiments of the present invention.

Next, a description will be given of a procedure for attaching the cuff 7 in the blood pressure measurement apparatus 1A with reference to FIGS. 6 and 7. FIG. 6 is a schematic diagram showing the procedure for attaching the cuff 7 in the blood pressure measurement apparatus 1A according to one or more embodiments of the present invention, showing how to insert the arm through the hollow portion of the upper arm insertion unit. Further, FIG. 7 is a schematic diagram showing a posture for measurement after the cuff is attached. It is to be noted that those figures are based on the assumption that the blood pressure value is measured on the left arm.

As shown in FIG. 6, in the case of measuring a blood pressure value by using the blood pressure measurement apparatus 1A according to one or more embodiments of the present invention, the main body portion 2 of the blood pressure measurement apparatus 1A is mounted on a desk 300 having a horizontal mount surface and a user 200 sits down on a chair 230.

The upper arm insertion unit 5 is rotated in an arrow A1 in the figure, and the arm rest 100 is moved rotatingly in an arrow B1 to such a position that the arm rest surface 100*a* and the elbow rest surface 3*a* may be roughly in plane with each other. The left arm is inserted through the hollow portion 5*a* of the upper arm insertion unit 5 as adjusting a tilt angle of the upper arm insertion unit 5. By further inserting the left arm deep through the hollow portion 5*a*, the cuff fitted in the upper arm insertion unit 5 deeply inserts the left arm until the cuff passes an arm 210 and faces an upper arm 220.

Next, the elbow of the left arm inserted through the hollow portion 5*a* is mounted on the elbow rest surface 3*a*, and the arm 210 is mounted on the arm rest surface 100*a* to provide a measurement posture shown in FIG. 7. It is to be noted that in this case, the upper arm insertion unit 5 rotates in an arrow A2 direction in the figure as following the movement of the left arm and finally stops at an angular position that corresponds to the tilt angle of the upper arm 220 of the left arm.

(State of Upper Arm 220 and Arm 210 in Measurement Posture)

Figure 8:
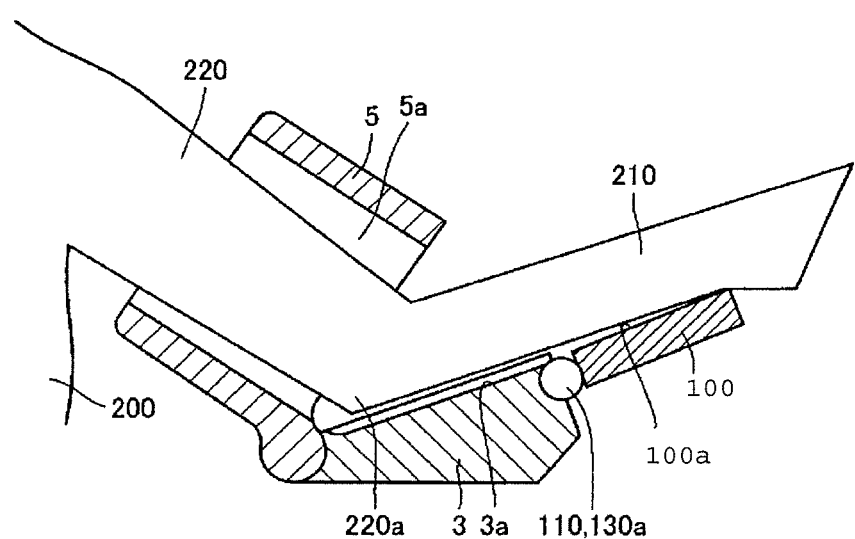
FIG. 8 is a schematic diagram showing a state of an upper arm and an arm during measurement in a case where the posture of the cuff in the blood pressure measurement apparatus is good according to one or more embodiments of the present invention.

Next, a description will be given of a state of the upper arm 220 and the arm 210 in a measurement posture with reference to FIGS. 8 and 9. FIG. 8 is a schematic diagram showing a measurement state of the upper arm 220 and the arm 210 in a case where the measurement posture is good, and FIG. 9 is a schematic diagram showing a measurement state of the upper arm 220 and the arm 210 in a case where the measurement posture is not good.

In a case where, as shown in FIG. 8, the measurement posture of the user 200 is good, that is, an elbow 220a of the left arm is mounted on the elbow rest surface 3a and the arm 210 is mounted on the arm rest surface 100a, the upper arm 220 is positioned roughly at the midsection of the hollow portion 5a of the upper arm insertion unit 5. Further, no unnecessary force is applied on the arm 210, so that the arm rest 100 does not flex downward. As a result, the cuff can be wound around the upper arm 220 properly, so that accurate blood pressure measurement results can be obtained.

Figure 9:
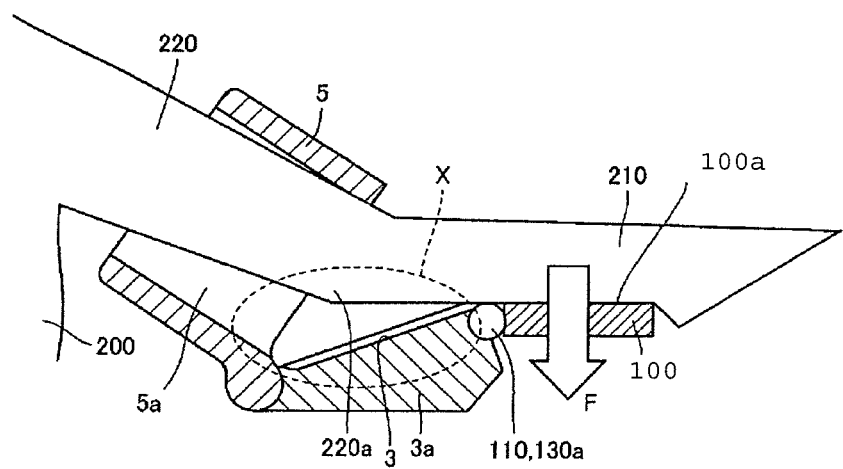
FIG. 9 is a schematic diagram showing a state of an upper arm and an arm during measurement in a case where the posture of the cuff in the blood pressure measurement apparatus is not good according to one or more embodiments of the present invention.

In a case where, as shown in FIG. 9, the measurement posture of the user 200 is not good, that is, an elbow 220a of the left arm is separate from the elbow rest surface 3a (region enclosed by X in the figure), unnecessary force F is applied on the arm 210, so that the arm rest 100 flexes downward. In this state, the upper arm 220 deflects upward in the hollow portion 5a of the upper arm insertion unit 5. Therefore, even if the blood pressure is measured in this state, accurate blood pressure measurement results cannot be obtained.

Figure 10:
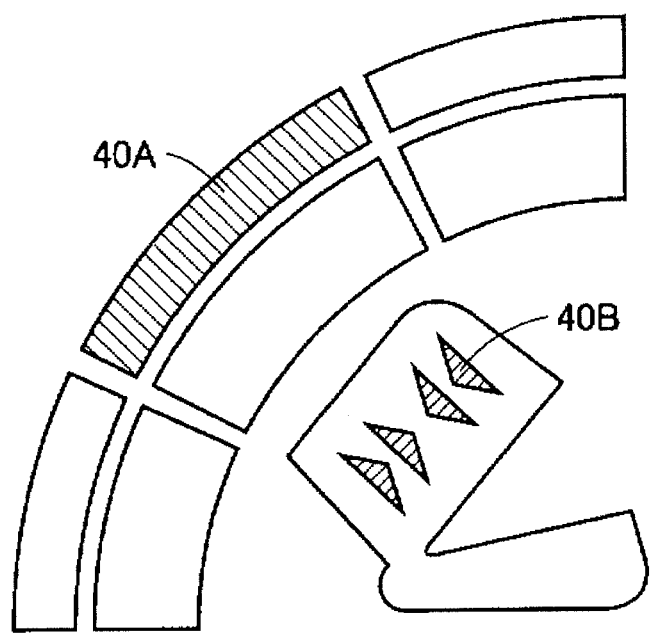
FIG. 10 is an illustrative view showing one example of informing means in the blood pressure measurement apparatus according to one or more embodiments of present invention.

Accordingly, in the measurement state shown in FIG. 9, the downward flexure of the arm rest 100 is detected by the flexure detection means 110 so that the user 200 may be supplied with information to that effect on the display unit 4B. By providing a partially color changing display 40A or a blinking display 40B on the display unit 4B as shown in FIG. 10, information about the bad measurement posture is sent to the user 200 to call the user's attention to the bad measurement posture.

Further, one or more embodiments of the present invention makes an announcement such as "Measurement posture is not good" or informs the user of a low reliability level in the measurement result. Moreover, one or more embodiments of the present invention uses a control method of permitting the CPU 40 to disable blood pressure measurement during a time when the flexure detection means 110 is detecting a downward flexure of the arm rest 100.

As described above, in the blood pressure measurement apparatus 1A according to one or more embodiments of the present invention, in a case where the elbow is mounted on the elbow rest surface 3a and the arm 210 is mounted on the arm rest surface 100a in a good measurement posture of the user 200, an unnecessary force is not applied to the arm 210, so that the arm rest 100 does not flex downward. However, if the measurement posture of the user is not good, an unnecessary force is applied to the arm 210, so that the arm rest 100 flexes downward.

The downward flexure of the arm rest 100 is detected by the flexure detection means 110, which can inform the user 200, on the display unit 4B, that the measurement posture is not good. As a result, the user 200 is prompted to assume a good measurement posture, thereby enabling accurate blood pressure measurement results to be obtained.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

Description of Reference Numerals
1A blood pressure measurement apparatus
2 main body portion
2a rotary coupling mechanism
3 main body portion casing
3a elbow rest surface
4A operation unit
4B display unit
5 upper arm insertion unit
5a hollow portion
6 upper arm insertion unit casing
7 cuff
8 organism compressing air bladder
20 organism compressing air system
21 air pump
22 air valve
23 pressure sensor
26 air pump drive circuit
27 air valve drive circuit
28 amplifier
29 ND converter
40 CPU
40A display
40B blinking display
41 memory unit
100 arm rest
100a arm rest surface
110 flexure detection means
130 support plate
130a rotary shaft
140 base member
200 user
210 arm
220 upper arm
220a elbow
230 chair
300 desk

The invention claimed is:

1. A blood pressure measurement apparatus comprising:
an upper arm insertion unit comprising a hollow portion through which an upper arm of a user is axially inserted from a front side and a main body portion to which the upper arm insertion unit is coupled;
an elbow rest surface provided on an upper surface of the main body portion,
wherein the elbow rest surface is an elongated surface that is directly connected to the main body portion; and
an arm rest comprising an arm rest surface provided on a rear side of the elbow rest surface so that an arm of the user is mounted thereon,
wherein the arm rest has a flexure detection means configured to detect a downward flexure of the arm rest in a condition where the arm of the user is mounted on the arm rest,
wherein the blood pressure measurement apparatus comprises an informing means which is configured to inform the user that the downward flexure of the arm rest is detected when the downward flexure of the arm rest is detected by the flexure detection means,
wherein the arm rest is coupled to the main body portion in such a manner as to freely rotate around a rotary shaft, which is provided on a coupling portion with the main body portion, between a position where the arm rest surface comes close to the elbow rest surface and a position where the arm rest surface and the elbow rest surface are roughly in plane with each other, and
wherein the flexure detection means detects downward rotation of the arm rest surface below the elbow rest surface by using the position where the arm rest surface and the elbow rest surface are roughly in plane with each other as a reference.

2. The blood pressure measurement apparatus of claim 1, wherein when the downward flexure of the arm rest is detected, the informing means provides a display of a flexure detected state on a display unit mounted on the blood pressure measurement apparatus.

* * * * *